United States Patent [19]

Tong et al.

[11] Patent Number: 5,595,444
[45] Date of Patent: Jan. 21, 1997

[54] METHOD FOR DETECTING POOR MEAT QUALITY IN GROUPS OF LIVE ANIMALS

[75] Inventors: Alan K. Tong; Stephen D. M. Jones; Allan L. Schaefer, all of Lacombe, Canada

[73] Assignee: Her Majesty the Queen in right of Canada, as represented by the Department of Agriculture and Agri-Food Canada, Lacombe, Canada

[21] Appl. No.: 543,752

[22] Filed: Oct. 16, 1995

Related U.S. Application Data

[63] Continuation-in-part of Ser. No. 84,993, Jul. 2, 1993, Pat. No. 5,458,418.

[51] Int. Cl.$^6$ .................................................. G01N 25/00
[52] U.S. Cl. .............................. 374/45; 374/124; 99/493
[58] Field of Search ............................. 374/45, 124, 4; 99/493

[56] References Cited

U.S. PATENT DOCUMENTS

| | | | |
|---|---|---|---|
| 3,887,818 | 4/1976 | Button et al. | 250/340 |
| 3,948,249 | 4/1976 | Ambrosini . | |
| 3,991,744 | 11/1976 | Goodfield . | |
| 4,366,381 | 12/1982 | Fischer et al. | 374/124 |
| 4,788,427 | 11/1988 | LeRoy | 374/124 |
| 4,914,672 | 4/1990 | Hebrank | 374/124 |
| 4,995,398 | 2/1991 | Turnridge | 128/736 |
| 4,998,826 | 3/1991 | Wood et al. | 374/124 |
| 5,017,019 | 5/1991 | Pompei | 374/133 |
| 5,458,418 | 10/1995 | Jones et al. | 374/45 |

FOREIGN PATENT DOCUMENTS

| | | |
|---|---|---|
| 91/14180 | 9/1991 | WIPO . |
| 92/00523 | 1/1992 | WIPO . |

OTHER PUBLICATIONS

Clark et al., "The Application of Thermovision Techniques to Animals", Deutsche Tieraztliche Wochenachrift 79:292–296 (1972).

Desroches, Garry B., "Stress Affected Livestock as Seen by Thermography", Proc. Int. Soc. Opti. Eng. 934: 120–129 (1988).

European Patent Application EP 0402 877 A1 (1990), Abstract Only.

Frens, J., "The Influence of Skin Temperature on Thermorequlation", In N. J. M. A. Tilburg, M. G. Strasbourg and E. F. J. R. (Ed.) Thermography. S. Karger, Basel P. 216–223 (1975).

Gariepy et al., "Early Prediction of PSE and DFD by Infrared Thermography on Live Animals", Proc. 33rd Int. Cong. Meat Sci. Tech II 403–406 (1987).

Gariepy et al., "Adipose Tissue Thermogenesis in Halothane Positive Pigs", Can. J. Anim. Sci. 69:1130 (1989).

Hayward et al., "Thermographic Evaluation of Relative Heat Loss Areas of Man during Cold Water Immersion", Aerospace Medicine, pp. 708–711 (Jul. 1973).

Hayward et al., "Thermal Balance and Survival Time Prediction of Men in Cold Water", Can. J. Physiol. Pharmacol. 53:21–32 (1975).

Houdas et al., "Environmental Factors Affecting Skin Temperatures", In N. J. M. A. Tilburg, M. G. Strasbourg and E. F. J. R. Both (Ed.) Thermography, S. Karger, Basel P. 157–165 (1975).

Jones, et al., "The Effects of Fasting and Transportation on Beef Cattle. 2. Body Component Changes, Carcass Composition and Meat Quality", Lives. Prod. Sci. 20:25–35 (1988).

Jones et al., "Factors Influencing the Commercial Incidence of Dark Cutting", Can. J. Anim. Sci. 69:649–654 (1989).

Kenny et al., "The Physiological and Behavioural Responses of Crossbred Friesian Steers to Shorthaul Transport by Road", Lives. Prod. Sci. 17:63–75 (1987).

Lamarque et al., "Etudthermographique Experimentale en Pathologic Artevielle Peripherique", Ann. Radiol. 18:513–523 (1975).

Murray et al., "Characteristics of the Meat Quality of a Halothane–Positive Line of Swine", Can. J. Animal. Sci. 68:1168 (1986).

Sather et al., "The Development of a Halothane Sensitive Line of Pigs"., Can. J. Anim. Sci. 69:323–331 (1989).

Schaefer et al., "Infrared Thermography in the Three Lines of Pigs", Can. J. Anim. Sci. 67:1181–1182 (1987).

Schaefer et al., "The Effects of Fasting and Transportation on Beef Cattle 1. Acid–Base–Electrolyte Balance and Infrared Heat Loss of Beef Cattle", Lives. Prod. Sci. 20:15–24 (1968).

(List continued on next page.)

*Primary Examiner*—Diego F. F. Gutierrez
*Attorney, Agent, or Firm*—Finnegan, Henderson, Farabow, Garrett & Dunner, L.L.P.

[57] ABSTRACT

The invention provides methods of detecting poor meat quality in live animals using infrared thermography. Animals from a group of live domestic animals such as cattle or swine are scanned to produce thermographic images. The images are then statistically analyzed to determine a measure of central tendency such as the mean temperature for each animal's image and for all of the images in the group. A measure of dispersion from the measure of central tendency, such as standard deviation is determined. Then, animals are rejected as having a high probability of producing poor meat quality if the measure of central tendency for that animal's temperature differs from the measure of central tendency for the group by more than 0.9 standard deviations. Alternatively a set percent of animals are rejected, preferably up to 20%, these being animals whose measures of central tendency differ the most from the measure of central tendency for the group. When mean temperature is used as a measure of central tendency, the method is preferably practised by rejecting animals whose mean temperature differs from the group mean temperature by more than 1.28 times the standard deviation for the group. The method is particularly useful in detecting high probability of poor meat quality in groups of animals in an antemortem environment which have mean temperatures significantly above or below the normal surface temperatures for unstressed animals.

23 Claims, No Drawings

OTHER PUBLICATIONS

Schaefer et al., "The Effects of Fasting and Transport on Acid–Base Balance, Infrared Heat Loss and Muscle Quality of Beef Cattle", Can. J. Anim. Sci. 67:1181–1182 (1987).

Schaeffer et al., "Infrared Thermography of Pigs with Known Genotypes for Stress Susceptibility in Relation to Pork Quality", Can. J. Animal Sci. 69: 491–495 (1989).

Scott et al., "What Effect Does Transportation Have on Heat Loss in Cattle?", Lacombe Research Highlights, 20–21, (1991).

Scott et al., "Assessment of the Effect of Transportation of Heat Loss in Cattle by Thermographic Analysis", Can. Soc. Anim. Sci. Annual Meeting, Jul. 5–9, 1992.

Stephan et al., "Measurements of Surface Temperature by Infrared Thermography in Veterinary Medicine"(preliminary report), Dtach. tieraztl. Wachr. 78:330–332. (No date).

Stephens, D. B., "Stress and its Management in Domestic Animals: A Review of Behavourial and Physiological Studies Under Field and Laboratory Situations", Adv. Vet. Sci. Comp. Med. 24:179:210 (1980).

Warris P., "Live Animals Marketing Effects on Carcass and Meat Quality", Proceedings P 7–41, In Work Planning Meeting and Meat Quality, Agric. Can. R. P. S. Otawa (1986).

METHOD FOR DETECTING POOR MEAT QUALITY IN GROUPS OF LIVE ANIMALS

CROSS-REFERENCE TO RELATED APPLICATION

This is a Continuation-In-Part application Ser. No. 07/084,993, filed Jul. 2, 1993, now U.S. Pat. No. 5,458,418.

FIELD OF THE INVENTION

This invention relates to methods for detecting poor meat quality in groups of live animals, and more particularly to the use of infrared thermography for such purposes.

BACKGROUND OF THE INVENTION

In domestic animals, handling and transport are known to be potent stressors (Stephens, 1980: and Kenny et al., 1987). Such stresses are often termed "antemortem stresses". These stresses have been documented to bring about changes in many physiological parameters including thermoregulation (Frens, 1975; and Houdas et al., 1975). It is also well documented that such factors as handling, mixing, and transport in the preslaughter environment (the "antemortem environment") are causative agents of poor meat quality (Jones et al., 1989; Jones et al., 1988; Warriss, 1986). Primarily affected are such quality attributes as colour, moisture holding capacity, pH, toughness and texture. If the stress is severe enough, the animal's energy supply is taxed, which in turn may lead to poor or degraded meat quality, such as dark, firm and dry (DFD) or tough meat in beef cattle, or pale, soft and exudative (PSE) meat in swine The assessment of meat quality has always, by necessity, been done on post mortem analysis. To the inventors' knowledge, prior to their own invention, as set forth in U.S. application Ser. No. 084,993, filed Jul. 2, 1993, now U.S. Pat. No. 5,458,418. (PCT Application No. PCT/CA94/00383, published Jan. 12, 1995) there has never been a technology with a demonstrated capability to detect animals likely to produce poor meat quality. Arguably, the development or discovery of such a technology capable of predicting meat quality in live animals in the antemortem environment has significant value to the meat production industry, since preventative and restorative therapy can be initiated in those identified animals.

Infrared thermography (IRT) has been used in human medicine for some time for the diagnosis and study of such conditions as tumors and cardiovascular integrity (Clark et al., 1972) as well as hyperthermia (Hayward et al., 1975). In domestic animals, IRT has also been found useful for diagnosing such conditions as vascular lesions in pigs (Lamarque et al., 1975) and leg injuries in horses (Clark et al., 1972).

The patent literature discloses the use of IRT for several purposes. U.S. Pat. No. 3,877,818 to Button et al., discloses the use of IRT for determining fat content in meat (post mortem). U.S. Pat. No. 3,948,249 to Ambrosini teaches 8 the use of an infrared detector for identifying a cow in heat. U.S. Pat. No. 5,017,019 to Pompei discloses the use of radiation detectors to measure temperature differentials in animals.

The inventors have been involved in previous studies using IRT with live animals. Initial studies by the co-inventors Jones, Schaefer and Gariepy suggested that IRT might be useful in identifying basic stress levels in cattle (Schaefer et al., 1987a, 1988) and in swine (Schaefer et al., 1987b; and Gariepy et al., 1987). The studies recognized that cattle having cooler surface temperatures as measured by IRT appear to have lower meat quality, while in pigs, poor meat quality was associated with very high surface temperatures. However, these studies fell short of teaching a method for reliably detecting the likelihood of poor meat quality in live animals.

There is a continuing need for a method of detecting, with acceptable accuracy, live animals susceptible to producing poor meat quality.

SUMMARY OF THE INVENTION

As set forth in their co-pending U.S. patent application Ser. No. 084,993, the inventors initially set out to develop a method for detecting poor meat quality in live animals with infrared thermography, by studying the anatomical sites and temperatures for different animals, along with the methods of analysing the thermographic data, so as to be sufficiently predictive of the relevant meat quality traits. By testing a large number of animals and breaking down the thermographic images by temperature zones, they discovered, surprisingly, that animals which went on to produce poor quality meat had infrared thermographs which were uncharacteristic in a particular test temperature zone. Compared to animals which produced high grade meat quality, the low grade meat quality animals were found to have thermographs which had higher proportions of the scan (measured by proportion of total pixel count) in temperature zones which were higher and lower than the test temperature zone. This discovery enabled the inventors to develop a reliable method for detecting for low meat quality in live animals.

The invention described in the inventors' earlier U.S. patent application extended to a method for detecting a high probability of producing poor meat quality in live domestic livestock, comprising the steps of:

(a) scanning the live animal with an infrared camera to produce a thermographic image;

(b) for cattle, determining the proportion of the scan falling within the test temperature range of 28°–32°±2° C.;

(c) for swine, determining the proportion of the scan falling within the test temperature range of 24°–26°±2° C.; and (c) rejecting the animal as one having a high probability of producing poor meat quality if the proportion of the scan falling within the test temperature range is lower than that falling outside the test temperature range.

In further work relating to the present application, the inventors discovered that the above method could be improved to reject animals having a high probability of producing poor meat quality with greater precision, particularly when the animals were part of an "atypical" group of animals. Atypical groups of animals were discovered having infrared temperature profiles which were considerably hotter or colder than the normal surface temperatures for animals of that species. For domestic cattle, that normal temperature is about 28°–32° C., while for swine, that normal temperature is about 24°–26° C. In the antemortem environment, such animals arrive as groups, such as a truckload, having experienced similar environments in either or both of the origin feedlot or farm, and the type and extent of antemortem stress conditions, such as time and extent of transport. Such groups of animals were discovered to have group mean temperatures, which, although different from the normal surface temperatures, did not necessarily indicate a very high incidence of poor meat quality. In such circumstances, the method of the inventors' earlier patent application might reject the entire group of animals as having a high probability of producing poor meat quality. While this was not incorrect, because animals in these groups on a whole had a higher probability of producing poor meat quality compared with groups which had a more normal mean temperature, the inventors set out to determine whether a more precise prediction of poor meat quality could be achieved.

The inventors discovered that the thermographic images from these atypical groups of animals can be statistically analyzed in order to reject animals whose temperature differed significantly from a norm for the group, such as a group mean temperature. More particularly, the inventors discovered that animals having a high probability of producing poor meat quality can be more precisely detected if the animals are processed as a group of animals which have experienced a similar environment prior to scanning. Animals whose thermographic images vary significantly from the norm, as determined from a statistical measure of central tendency of the temperatures for the group, were discovered to contain a high proportion, if not all, of the animals which produce poor meat quality.

The most preferred measure of central tendency used for the thermographic images is the mean temperature, both for the image of each individual animal, and the images for the group. However, other measures of central tendency including median or mode may also be used. To assist in determining significant departure from the norm, a measure of dispersion from the measure of central tendency, such as standard deviation (SD), is preferably determined.

In accordance with the present invention, up to 20% of the animals are rejected as having a high probability of producing poor meat quality, the rejected animals being those whose measures of central tendency differ the most from the measure of central tendency for the group. Preferably, in rejection, an animal is rejected if its mean temperature differs from the group mean temperature by more than 1.28 times the standard deviation for the group. This effectively rejects the upper 10 percent and lower 10 percent of the outliers (i.e. animals whose mean temperatures are most distanced from the group mean temperature) from a bell shaped normal population curve, i.e. a standardized population of animals having a mean of zero and a standard deviation of 1.

The method of the present invention can be practised by rejecting a greater number or lesser number of outliers, say as much as 36 percent for stress sensitive groups, or only 5 percent for lower stressed groups. This is largely a matter of economics to be determined by the commercial meat packers. However, as will be evident to those skilled in the art, rejecting 20 percent as outliers if the poor meat quality animals are all within the upper and lower 5 percent, is inefficient. Generally, rejecting 5–20% as outliers is likely to be economical for most meat packers. The inventors have demonstrated that rejecting the upper and lower 10 percent as outliers (i.e. up to 20 percent) will likely include all of the dark cutters in a group of beef cattle and elk. If economics dictate, the method can be practised by rejecting only the upper and lower 5 percent as outliers (i.e. up to 10 percent, or animals whose mean temperature differs from the group mean by more than 1.65 SD). For swine, the inventors have demonstrated that rejecting up to 36% as outliers includes poor meat quality animals in groups predisposed to stress. In a normal genotype pig, rejecting up to 10–20% should be sufficient.

Broadly stated, the invention provides a method for detecting those animals from a group of live domestic animals which have a high probability of producing poor meat quality, comprising:

scanning an area of each animal of the group of live domestic animals with an infrared camera to produce a thermographic image for each animal;

for each animal's thermographic image, determining a measure of central tendency for the temperature;

for the images from the group of live domestic animals, determining a measure of central tendency for the temperatures from all of the images; and rejecting as animals having a high probability of producing poor meat quality, up to twenty percent of the animals, the rejected animals being those whose measures of central tendency differ the most from the measure of central tendency for the group.

Although the method has been demonstrated for groups of animals having atypical temperature profiles, specifically beef cattle having a group mean temperature significantly below the normal 28°–32° C. temperature, it also has application for groups of animals having group mean temperatures above that norm. The method also has application for groups of animals having more normal temperature profiles, for example groups of animals having a group mean temperature in the normal temperature range for that animal species.

Furthermore, although the method has been demonstrated for groups of beef cattle, elk and swine, it has application for all live domestic animals. For swine, the method is particularly useful for groups of animals having a group mean significantly above or below the normal temperature range of 24°–26° C., although the method is also useful within that temperature range.

Furthermore, while the method of detection and rejection is based on a group of animals whose temperature distributions fit a normal bell shaped curve, the method also has application for groups whose temperature distributions are non-homogeneous, i.e. which are skewed toward either the higher or lower temperatures.

The term "domestic animals", as used herein and in the claims, is meant to include domestic ruminant and monogastric animals, including swine, horses, cattle (Bos taurus and Bos indicus) and domestic ungulates such as bison, sheep, lamb, deer, moose, elk, caribou and goats.

The term "thermographic image" as used herein and in the claims, is meant to include a scan output in the form of either or both of a visual image and corresponding temperature data. The output from infrared cameras used for infrared thermography typically provides an image comprising a plurality of pixel data points, each pixel providing a temperature data point which can be further processed by computer software to generate for example, mean temperature for the image, or a discrete area of the image, by averaging the data points over the number of pixels.

The term "group of live domestic animals" as used herein and in the claims is meant to include a minimum of three animals from the same or similar species of animal which have been subjected to the similar types and/or duration of antemortem stresses. Preferably a minimum of 10 animals comprise a group. More preferably, and more typically in the industry, a group of animals will include about 40 or more animals from one or more truck or train-car loads which have originated from one farm or feedlot, or which have originated from different farms/feedlots, but which have been transported a significant distance for a similar duration of time.

The term "measure of central tendency" as used herein and in the claims is a statistical measure of a point near the centre of a group of data points. Without limitation, the term includes the mean, median and mode. The mean temperature is the most preferred measure of central tendency used in the present method. For each animal's image, the mean temperature is determined from the average pixel temperature for a discrete area of that animal that has been scanned. Just by way of example, the area between the atlas and thoracic vertebrae in a dorsal scan of beef cattle may be the discrete area scanned. The mean temperature determined for each animal's image is the arithmetic mean of the pixel temperatures for the discrete area, identified as say the 70×90 pixels of the image in that discrete area. For the group of live domestic animals, the mean temperature is determined from the individual animal mean temperatures determined from the images taken of the consistent discrete area of the animals scanned.

The term "measure of dispersion" as used herein and in the claims is meant to include statistical measures of spread from the measure of central tendency for the group. Preferred measures of dispersion when the measure of central tendency is the mean, include variance, standard deviation and coefficient of variation. Most preferred is "standard deviation". Definitions of these statistical terms may be found in standard statistic texts, one such text being Steel, R and Torrie, J, 1980 2d edition, Principles and Procedures of Statistics, A Biometrical Approach, McGraw-Hill, New York, which definitions are incorporated herein be reference.

The term "standard deviation" as used herein and in the claims is the positive square root of the variance for the group, the variance being the arithmetic mean of the squares of the deviations of the individual values from their arithmetic mean. For a group of live domestic animals, wherein the measure of central tendency being used for each individual animal's image is the mean temperature ($\mu_i$), and wherein the measure of central tendency being used for the group of all the animal images is the group mean temperature ($\mu_g$), then the standard deviation (SD) for a group of n animals is:

$$SD = \sqrt{\frac{\sum_{i=1}^{n}(\mu_i - \mu_g)}{n}}$$

DESCRIPTION OF THE PREFERRED EMBODIMENTS

In the inventor' previous patent application, the method of detection with infrared thermography was proven effective in detecting animals having a high probability of producing poor or degraded meat quality on subsequent slaughter. There, in a test group of 54 bulls, the method proved to be greater than 80% effective in advance detection of dark cutting. This is a very high accuracy rate. Once animals were detected, they could be treated to improve meat quality. For instance, a composition for such a method of restoring degraded meat quality and improving carcass yield loss is disclosed in U.S. application Ser. No. 08/084,989 filed Jul. 2, 1993 by Jones et al., now U.S. Pat. No. 5,458,418.

Infrared thermography equipment (camera, analytical software) is known in the art. Preferably, animals, or relevant anatomical sites, are scanned at relatively close range (1–3 m) at an angle between about 45°–90° from the horizontal surface of the animal.

Software is available for analysing the thermographic images produced from the camera. An exemplary software package is Viewsoft (Version 2.0 Viewscan Ltd., Concord, Ontario, Canada). In the inventors' previous application the images were preferably analyzed to determine the proportion of a scan that fell within a particular temperature range (ie. proportion of total pixels of a defined area which fell within a particular temperature range). The same or similar software can be used in the practise of the method of the present invention to calculate the statistical measures of central tendency and dispersion.

Preferred conditions of scanning were reported in the inventor's previous patent application, and are applicable to the method of this invention, including, for different animal types, the relevant anatomical sites, the type of scan view, and the timing of the detection.

For all live domestic cattle, scanning is preferably conducted within about 6 hours of transport or within 24 hours of slaughter. Scanning after 6 hours of transport may still be conducted, however, the stressed animals having cooler or warmer thermographs than the normal range, will be generally cooler, making detection somewhat less precise. However, for animals which are held in lairage preslaughter, the method is preferably practised within 24 hours of slaughter.

For cattle and elk, a dorsal view is most preferred. This is likely also the most accessible and economical view. However, side views are also efficacious. The most revealing anatomical site is the dorsal surface between the atlas and thoracic vertebrae. However, side views of trunk, head and extremities are also efficacious.

Scanning swine by infrared thermography showed that a dorsal view is most preferred. The most revealing anatomical sites include the dorsal area between the atlas and thoracic vertebrae, most preferably including the intrascapular area between the atlas and cervical vertebrae.

While the IR detection method of this invention is preferably practised with computer data analysis of the statistical measures, it is also amenable to displaying the images, in order to provide the operator with a more immediate "feel" for the data, as it is being collected. Distinctive colours or grey tones may be assigned by computers to the test temperature ranges of the scan and to the non-test temperature ranges (preferably every 1°–2° temperature range has a different colour). The thermographs are displayed on a computer monitor, such that a human operator can determine if the animals are generally warmer or cooler than the norm.

The practise of the method of the present invention will differ from one commercial packing plant to another, depending on the overall automation level available or desirable. Generally, the groups of live domestic animals arrive at the plant in truckloads of about 40 or more animals. Each animal of the group is scanned with the infrared camera positioned to view a relevant, discrete and consistent anatomical site. The digitalized data output from the camera is used to determine the mean temperature for each animal's image, the mean temperature for the group of animal images, and the average deviation, or more preferably the standard deviation. Animals are rejected after comparing the individual animal mean temperature with the group mean temperature. Animals whose mean temperature differs from the group mean by more than about 0.9 standard deviations, or more preferably, by more than 1.28 standard deviations are rejected as animals having a high probability of producing poor meat quality. To facilitate the locating and separating of the rejected animals, each animal may be marked or tagged prior to scanning. Bar code tags may be advantageously used, since this allows for automated rejection by running the animal through a bar code scanner. Alternatively, animals are rejected as the 5–36%, most preferably as the 10–20%, whose mean temperatures differ the most from the group mean. Any measure of dispersion from the group mean can be used in this determination, including variance and coefficient of variation, but most preferably standard deviation.

The method may be practised by scanning less than the entire group of animals, for example 10 or more animals, in order to determine the initial statistical basis for rejecting the animals. The remaining animals in the group could then be scanned and virtually immediately rejected in accordance with the animal's calculated mean temperature. With computer analysis, the statistical analysis for the group can be continuously, and virtually instantaneously updated with each animal scanned. While this continuous method may be less precise, at least for the early animals scanned, it is less time consuming in that the animals may be rejected in a single scan once the group statistics were established. For very large feedlots a group of live animals may comprise hundreds of animals. A first truckload of these animals, comprising for example 45–50 animals, can suffice to determine the group mean and standard deviation as the basis for rejecting animals from the remaining truckloads.

Rejected animals likely to produce degraded meat quality may be isolated for later treatment or lower sale value.

The method of the invention is illustrated in the following non-limiting examples. The first three examples illustrate the method of the inventors' previous patent application, but are repeated here to illustrate the applicability of IR thermography to different animal species, scanning different anatomical sites and the like. Although the method of the present invention differs from that of Examples 1–3, certain aspects of the examples are applicable. Preferred embodiments of the method of the present invention is illustrated in Examples 4–6.

EXAMPLES

In Examples 1–3 the inventors developed infrared thermographic detection technology under simulated management and transportation practices normally experienced by market cattle. For example, a producer may transport cattle directly to an abattoir. Alternatively, a producer may transport cattle to an auction mart, and leave them overnight in lairage for sale the next day. After sale, the animals might be shipped again to a feedlot or to an abattoir, where they might be left again overnight. Thus the timing between the feedlot, transport and slaughter might be anywhere from an hour to several days. The timing affects the thermographic image of the animal.

EXAMPLE 1

This example reports early work with cattle using infrared scans taken as total animal side views just prior to stunning. In this example, 30 steers and 21 heifers (1 to 1.5 years old) were penned separately, fasted for 24 hours, and divided into three treatment groups. The control group, Treatment 1, was not mixed by sex before being transported 3 km to the research centre. Including time in lairage, the animals were off feed for 24 hours. The second group, Treatment 2, was mixed by sex and transported for 320 km (6 hours) prior to a lairage period of 18 hours. Animals were off feed for 48 hours altogether. The third group, Treatment 3, was treated the same as Treatment 2, except that the animals received an additional 320 km (6 hours) of transport and were in lairage for another 18 hours. They were off feed for a total of 72 hours. Following the lairage period, animals were stunned and slaughtered at the Research Centre where carcass composition and meat quality were analyzed.

Infrared pictures or scans were taken of each animal just prior to stunning. The infrared thermal images (scans or thermographs) were taken with an Agema model 782 camera (AGA, Lidingo, Sweden). Subsequent resolution and printing of the individual thermographs was accomplished using Viewscan software (Viewscan Ltd, Concord, Ontario, Canada) as set out below.

The video signal from the camera was converted to digital data with a A/D converter before being processed by a computer as follows. The image was saved as a raw, uncalibrated data file. The area of the image itself was divided into 7140 pixels or pieces of information. The raw pixel data was digital data proportional to voltage signals from the IR camera. In order to analyze the thermograph, the digital data was converted to temperature data using a calibration procedure with the Viewsoft software. After calibration, the pixels were displayed in fifteen different colours plus a background colour, representing fifteen temperature ranges of $1.2\pm0.2°$ C., ranging from 15.0 to 32.0° C.

The Viewsoft software allowed for analysis of the pixel data by different zones or by the entire image. Seven zones were identified as: Zone 0—whole image, including background, Zone 1—whole body of animal excluding background, Zone 2—trunk of the animal excluding extremities, Zone 3—front trunk from the shoulders to the midline, Zone 4—back trunk from the midline to the tail, Zone 5—head and neck, and Zone 6—extremities, including legs and tail. The following information was obtained for each zone using the Viewsoft software: absolute pixel counts and pixel counts as a percentage of the total pixels in the zone falling into each temperature range; maximum and minimum temperatures in the zone; the overall range of temperatures in the zone; the median, the mean, and standard deviations of temperatures in the zone; the total area of the zone (in pixels); and the area of the zone as a percentage of the total image area. The temperatures were grouped into larger temperature ranges to analyze the data. The four temperature ranges were: (1) 10.0–18.0, (2) 18.0–23.0 (3) 23.0–28.0 and (4) 28.0–36.0. The temperatures in each body zone were grouped into the four ranges. The number of pixels falling into each range was expressed as a percentage of the total number of pixels in that zone.

Since heat loss from the body surface may vary with location on the body, the thermograph of the animal's body was divided into three zones for analysis, the trunk, the head, and the extremities. In each body zone, the area covered by each temperature range was expressed as a percentage of the total visible area.

The three treatments resulted in different thermographic patterns. The animals with the greatest degree of transport stress had the greatest proportions of pixels counts in the cooler ranges.

The cattle with the greatest level of stress also showed altered meat quality traits observed as objective colour and shear values. The meat quality assessment was conducted according to the methods described by Jones et al., 1988. The cattle with the most degraded meat quality were those which had received the greatest stresses. The meat quality data is set out in Table 1.

TABLE 1

Effect of transport and handling in market weight cattle on the objective colour and shear values (toughness)

| Meat Quality Value | Treatment | | |
|---|---|---|---|
| | 1 | 2 | 3 |
| Shear (kg) | 5.08 a | 6.75 b | 8.23 b |
| Colour | | | |
| L* | 38.03 a | 36.73 b | 36.02 b |
| a* | 18.50 a | 17.88 ab | 17.27 b |
| b* | 14.25 a | 13.14 b | 12.88 b |

Note:
a,b $P < 0.05$
(*C.I.E. colour system)

EXAMPLE 2

This example is included to demonstrate the efficacy of the method of the present invention in detecting poor meat quality in swine using infrared thermography. The IR scans were taken with a Thermovision 750 Serial #1066 camera with a 7 and 0 degree angle lens. Temperature measurements were made with a Taylor 9200 digital thermometer fitted with either a type J surface contact probe or an Exergen Microscanner to facilitate videorecording and electronic capture. Viewsoft version 2.00 software was used to analyze the thermographs.

Trial 1

Both barrows and gilts were used in this experiment. Two IRT scan procedures were used on the pigs. The first IRT image (A) was made of the pigs as they left their home pens. At this time the pigs were not mixed and were unstressed. The second image (B) was made of the pigs after they had been mixed with unfamiliar pigs and moved around the barn. This mixing and moving of pigs is common in the industry and constitutes a stress to the animals. The thermal images of the pigs were taken while the animal was in a small holding pen (squeeze). The animal was viewed from above and behind at a distance of approximately 0.7 meters with the 20 degree lens. The most revealing and useful angle scans were taken of the back and head enfilading at the spine at an angle of more than 45 degrees from the horizontal. The images were interfered in the neck or cervical region by a crossbar, visible in the thermographs.

The thermographs of 4 animals, with colours or grey tones assigned to temperature ranges were analyzed. It was evident that the animals receiving the greater stress had temperatures elevated above the 24°–26° C. range in the dorsal surface, specifically between the atlas and the cervical vertebrae, including the intrascapular area. The temperatures range in the thermographs was 21.7°–28.1° C., with 0.5° C. increments. The blue and purple temperature ranges were between 22.7° and 24.1° C. The black and dark green ranges were between 24.1 and 25.0. The light green ranges were between 25.0 and 25.9. The yellow range was between 25.9 and 26.4. The orange, bright purple and red ranges were between 26.4° and 28.1° C. With grey tones, the cooler temperatures were assigned darker tones and the warmer temperatures were assigned gradually lighter tones.

Trial 2

The purpose of this trial was to confirm the site specificity of heat production as was suggested by the above trial. This trial also tested this specificity in pigs known to produce a high incidence of poor meat quality when subjected to antemortem stress. The degree of stress induced in the pigs in this trial was controlled by the direct manipulation of stress hormones (adrenergic agonists).

The pigs in this trial were genetically stress-susceptible or halothane positive pigs (H+phenotype, nn genotype) as defined by Sather et al., 1989. These pigs are known to produce a high incidence (80%) of poor meat quality traits, including pale colour, soft, texture, exudative or high drip-loss pork and low pH (Murray et al., 1986).

The pigs were fitted with indwelling ear-vein catheters under aseptic conditions 24 hours prior to endocrine studies. On the day of experiments the pigs were anaesthetized with ketamine (Ketalar) at 20 mg per kg animal weight in accordance with guidelines established by the Canadian Council on Animal Care. It should be noted that ketamine anaesthesia was necessary in that a respiratory anaesthetic such as halothane would have induced malignant hyperthermia in these pigs. Following anaesthesia the pigs received an intravenous infusion of selected adrenergic agonists including dobutamine (Dobutrex, B1, 5.6 ug/kg/min for 30 minutes), and Clenbuterol (B2, 3.39 ug/kg/min for 30 minutes). In anaesthetized pigs, a series of sub cutaneous thermocouples (inserted approximately 2 cm) were placed along the spine from the cervical to the lumbar areas. These thermocouples were connected to a data-logger which recorded direct temperature readings every 30 seconds.

The results showed that a direct and controlled challenge of adrenergic agonists (stress hormones) in pigs known to produce poor quality pork was accompanied by an increase in the thermocouple temperature, particularly in the cervical (and occasionally lumbar but not thoracic) areas of the dorsal surface of the pig. This increase in temperature is consistent with the above trial showing IRT temperature increases in these same anatomical areas. The data also confirms that these thermal changes coincide with the production of poor pork quality, as the halothane positive pigs used in this trial are documented to produce approximately 80% poor pork quality.

EXAMPLE 3

This example illustrates an IR detection method using dorsal IR thermographs of bulls taken directly after transport. The camera and computer software were as in Example 1.

In this example data was collected on 54 crossbred yearling bulls weighing on average 500 kg. The animals had been raised on a conventional balanced silage-cereal grain diet with ad libitum access to water and iodized salt. The cattle were allocated to one of two treatments, balanced by breed and weight and designated as control or treated. The control animals remained on their normal diets and with familiar pen mates until the morning of the experiment. The cattle were then moved to a weighing facility, weighed, loaded onto a commercial cattle liner and transported a short distance (3 km) to the abattoir. The bulls were then unloaded into abattoir lairage pens, measuring approximately 3 m by 10 m for ½ to 2 hours before being scanned from above with an infrared thermography camera (as Ex. 1). The camera was placed approximately 2 m above the back of the animal and the scan was taken at approximately a 75 degree angle. Within 2 to 3 hours of being scanned, the animals were moved on into the abattoir premise and slaughtered as per conventional commercial practice.

The treatment animals were taken off of feed and water 24 hours before transport. In addition, the bulls were mixed from a minimum of 2 different and unfamiliar pens of cattle.

These time off feed and mixing conditions are common in auction mart and some feedlot operations, and constitute a stress to the animals. The treatment bulls received one hour of transport following morning weight collections. Once unloaded in the abattoir/lairage area the infrared scanning and slaughter procedures were completed in an identical manner to the control animals. Meat quality data was assessed as per the Canadian grading system (Dark cutters grading B4, or formerly a grade of B2 prior to institution of the new beef grading system in 1993). The thermographs for 32 animals were analyzed as set out below.

For animals in this study, 11 temperature ranges in were examined. These ranges (°C.) were as follows: 1=10.0–18.9; 2=18.9–20.8; 3=20.8–22.7; 4=22.7–24.6; 5=24.6–26.5; 6=26.5–28.4; 7=28.4–30.3; 8=30.3–32.2; 9=32.2–34.1; 10=34.1–36.0; 11=36.0–37.9.

Following statistical analysis of the data, it was learned that:

(a) greater than 80% of the treated cattle produced carcasses designated by the grading system as being B4 dark cutters;

(b) 40% of the pixel area from the control animals, but only 12% of the pixel areas of the treated animals, fell into temperature range 7;

(c) 30% of the pixel area of the control animals, but only 16% of the pixel area of the treated animals, fell into temperature range 8.

Animals within the temperature ranges 7 and 8, that is with higher pixel numbers in those ranges than outside those ranges were termed Group A. All of the animals in Group A proved to produce normal or non-dark cutting meat, with the exception of one animal, which proved to be a dark cutter. Groups B and C thermographs for animals outside the temperature ranges 7 and 8, that is with higher pixel counts outside the ranges than inside the ranges differed from the Group A thermographs. Group B thermographs were below (cooler than) the temperature ranges 7 and 8, while Group C thermographs were above (warmer than) the temperature ranges 7 and 8. All of the animals whose thermographs were in groups B and C proved to produce darker coloured meat (dark cutters) (with the exception of one animal (of the 24 in B and C)). By assigning colours or grey tones to the ranges, one is able to readily visually determine which animals are predominantly within or without the temperature ranges.

It is thus apparent that the majority of treated (stressed) cattle had a lower proportion of pixels in the ranges 7 and 8, and a higher proportion of pixels in the hotter or colder temperatures outside these ranges. Thus animals having a lower number of pixels in the temperature ranges 7 and 8 were more likely to be stressed and had a higher probability of poor meat quality.

EXAMPLE 4

The process of the present invention was demonstrated with a group of 135 live market weight beef cattle weighing about 500 kg each. The animals were scanned at a commercial packing plant after several hours of transport and/or lairage. The scans were performed in a manner similar to Example 1, using an Inframetrics 760 BroadBand camera (North Billerica, Mass.), with a 0.5×lens (40° wide, 30° vertical). The dorsal surface of each animal was scanned (5 ft from the surface) to provide a thermographic image. A rectangular area of each animal's image, approximately 70×90 pixels, starting at or near the thoracic vertebrae, was selected on each dorsal view of the digitized infrared thermographic image. The images were analyzed using TPI Image software (Ottawa, Ontario) on a Macintosh computer. The mean temperature of all pixels within this selected area was calculated for each of the 135 cattle. The group mean and standard deviation were calculated as 9.4° C. and 1.2° C., respectively. Animals were rejected as outliers likely to produce poor meat quality if their individual mean temperature differed from the group mean temperature by more than 1.28 times the standard deviation. The area under a bell shaped normal population curve (mean of zero and a standard deviation of unity) which is in the tails, differing from the mean by more than 1.28 SD, is 20 percent of the total area. Thus this method was chosen to reject as outliers, approximately the upper 10 percent and lower 10 percent (area under the curve) of animals from a standardized population having a mean of zero and a variance of 1. The two critical points for rejection were thus the group mean ±1.28× the calculated standard deviation, or 9.4+(1.28×1.2)=10.94° C. and 9.4−(1.28×1.2)=7.86° C. Thus, approximately 20 percent of the cattle, those with a mean temperature below 7.86° C. and above 10.94° C., were rejected as outliers that are likely to produce poor meat quality. The number of cattle rejected by this method from the group of 135 cattle was 31 (actual rejection percent was 23%).

After slaughter and meat grading as set forth in Example 1, (pH, Minolta color meter giving the CIE L*, a* and b* coordinates and carcass temperature measurements were recorded for the non-rejected cattle and the outliers. There were no dark cutting carcasses from the 104 non-rejected cattle. Of the 31 carcasses rejected as outliers, evidence from the objective quality measurements indicated that two of the animals had two or more objective measures (pH and a*, b*) that placed them in a dark cutting category. An additional two animals that were suspect of being in a dark cutting category on the basis of one of the measures (a*).

EXAMPLE 5

This example is included to demonstrate the IR thermographic detection method of the present invention with a group of 25 (n=25) market weight (92 kg) live swine.

The animals used in this experiment represented three genotypes normal, non-halothane gene carrier animals (denoted H—, n=8), heterozygote, halothane gene carrier animals (denoted H+−, n=9), and homozygote, halothane gene positive animals (denoted H++, n=8). Pigs carrying the stress susceptible gene (halothane gene) are known to produce a higher incidence of poor pork quality and are therefore a good research model for studying pork quality. The development of halothane gene lines as well as a description of their meat quality is described in detail by Sather and Murray, 1986, and Murray and Sather, 1989. Typically, pigs carrying the halothane positive gene produce pork displaying a higher degree of pale-soft-exudative properties, usually with a lower pH. Use of halothane positive pigs alloys a smaller population sample to be utilised and tested, however, the results from this experiment are predictive of the utility of the method in other swine populations. A description of pork quality is given in the publication by Agriculture Canada, 1984.

The animals used in this trial were raised at the Lacombe Research Centre, Alberta, Canada, on conventional swine diets and received a short transport and handling treatment (20 minutes) on a commercial livestock carrier before arriving at the Meat Research Centre abattoir, located at the Lacombe Research Centre. Infrared thermographs of the dorsal (back) area were collected within 1 hour of arrival at the abattoir, as described in Example 2. An Agema IRT camera (model 782, AGA, Lidingo, Sweden) and graphics package (IBM enhanced AT computer and Viewscan Software, Viewscan Ltd, Concord, Ontario, Canada) were used to collect and analyze the data. Mean temperatures were determined for each image and for the group of images. Standard deviation was also determined. The mean temperature for the group was 25.51° C., and the standard deviation was 2.33. Following slaughter, pork quality was assessed on all animals using conventional methods as described in the Agriculture Canada 1984 publication.

The data and meat quality analyses are shown in Tables 2 and 3 below. In Table 2, animal identification numbers, genotypes (H—, H+—, H++), and mean dorsal temperatures from individual scans are given. Apparent from Table 2 is the observation that animals displaying the lowest and highest dorsal mean temperatures (approximately above and below 0.9 standard deviations of the group mean, representing 36% of the animals) are from either halothane positive or carrier genotypes. Only one of these outliers was a non carrier or non halothane positive pig. In other words, the upper and lower tails of a distribution curve for this data, representing the data points more than 0.9 standard deviations from the group mean included the animals known to produce higher incidence of poor pork quality attributes on a population basis. This is also supported by the comparison of average pork quality traits of the animals in the outlier tails with those of the normal pigs, not carrying the halothane gene, as shown in Table 3. Pigs displaying upper and lower temperatures had lower pH, higher shears (toughness), and greater drip loss than normal pigs.

It will also be noted from Table 2, that the distribution of the data points in this experiment are non-homogeneous, that is they are not evenly distributed from the mean. The halothane gene is known to predispose pigs to a condition of malignant hyperthermia which would cause more pigs to produce higher dorsal mean temperatures under stress, such as handling and transport (see Mitchell and Heffron, 1982). Thus, although the data is skewed toward the warmer temperatures, the rejection method of the present invention is operative, whether rejecting as a percentage differing from the group mean, or as a factor of the standard deviation.

This example thus demonstrates the method of the present invention by rejecting swine whose mean temperatures vary by more than 0.9 standard deviations from the group mean or the 36% outliers, as those animals likely to produce poor meat quality. In a population of non stress susceptible pigs, ie pigs not carrying the halothane gene, the proportion of animals falling into the outlier regions should be smaller, so the method might be practised economically by rejecting up to approximately 20% of the animals as outliers, or by rejecting the animals whose mean temperature differs by more than 1.28 standard deviations, or some other factor found to be economical.

TABLE 2

Distribution of Dorsal Infrared Temperatures, Animal ID and Genotype For Pigs Used in The Current Study

| | Temp. °C. | | | | | | | | | |
|---|---|---|---|---|---|---|---|---|---|---|
| | 19.0 | 20.0 | 21.0 | 22.0 | 23.0 | 24.0 | 25.0 | 26.0 | 27.0 | 28.0 |
| Temp °C. | 19.0 | | 21.0 | 22.9 | 23.6 | 24.8 | 25.0 | 26.6 | 27.4 | 28.0 |
| ID | 26404 | | 25001 | 21602 | 30402 | 27101 | 21608 | 23902 | 23901 | 22202 |
| Gene. | H— | | H+— | H+— | H— | H+— | H++ | H— | H— | H+— |
| Temp | | | | 22.8 | 23.0 | | 25.8 | 26.6 | 27.7 | 28.2 |
| ID | | | | 22506 | 25004 | | 21504 | 27403 | 23603 | 21306 |
| Gene. | | | | H++ | H+— | | H++ | H— | H+— | H++ |
| Temp | | | | | | | 25.9 | 26.5 | 27.8 | |
| ID | | | | | | | 22101 | 30209 | 21405 | |
| Gene. | | | | | | | H++ | H— | H++ | |
| Temp | | | | | | | 25.2 | 26.8 | 27.5 | |
| ID | | | | | | | 23502 | 22209 | 22408 | |
| Gene. | | | | | | | H+— | H+— | H++ | |
| Temp | | | | | | | 25.7 | 26.7 | 27.6 | |
| ID | | | | | | | 28806 | 22601 | 24006 | |
| Gene. | | | | | | | H— | H++ | H+— | |
| Temp | | | | | | | 25.7 | | | |
| ID | | | | | | | 25005 | | | |
| Gene. | | | | | | | H— | | | |

TABLE 3

Meat Quality Traits in Normal Pigs and in Pigs Screened as Outliers (above and below 0.9 standard deviations of the mean) Based on Dorsal Infrared Temperatures.

| Meat Quality Trait | Normal Pigs (H—, n = 8) | Lower Dorsal Temp (below 0.9 SD, n = 5) | Upper Dorsal Temp (above 0.9 SD, n = 4) |
|---|---|---|---|
| pH 45 | 6.26 | 5.98 | 5.85 |
| pH unit | 5.61 | 5.59 | 5.56 |
| Shear | 5.85 | 6.2 | 6.8 |
| L* | 50.2 | 51.4 | 51.1 |
| a* | 7.45 | 7.7 | 7.9 |
| b* | 2.1 | 2.9 | 2.7 |
| Expressible Juice | 5.27 | 5.14 | 5.84 |
| Drip Loss % | 2.11 | 2.95 | 3.09 |
| Mean Dorsal Temp | 25.1 | 21.7 | 27.9 |

EXAMPLE 6

This example illustrates the method of the present invention with a group of live elk animals (wapiti).

Twelve adult (2–6 year old, male) wapiti were used in the experiment. All animals received 4–6 hour transport to the Lacombe Research Centre prior to being held overnight in lairage. All animals received 0.5–1 kg of an electrolyte pellet pre-transport (NUTRI-CHARGE, trade mark of Agriculture Canada), and six of the animals were given an additional liquid electrolyte drink overnight at the abattoir preslaughter. The animals were scanned with IRT cameras, dorsal views, as set out in Example 3, immediately before slaughter. The wapiti were subsequently stunned by captive bolt, processed and meat quality was assessed on the Longissimus muscle.

Statistical analysis of the thermographic images, showed mean dorsal temperatures ranged from 28.2°–33.5° C., with a group mean of 31.1 and a standard deviation of 1.2 from the mean. The upper 10% (one animal) displayed a mean dorsal temperature of 33.49. The lower 10% (one animal) displayed a mean dorsal temperature of 28.21.

Meat quality analysis, showed a group average for pH of 5.80 (L.D. muscle or longissimus dorsi at 24 h post stunning), $L^*$ colour was 29.8, $a^*$ was 14.4, and $b^*$ was 5.4. The upper and lower temperature animals identified by IRT scans displayed pH, $L^*$, $a^*$, $b^*$ values of 5.82, 28.4, 12.9, 4.6 for the upper animal, and 5.73, 28.9, 13.5, 4.6 for the lower animal. Thus, the upper and lower temperature animals displayed darker coloured meat than the average and higher or lower pH values than the average.

Thus, by rejecting either the approximately 20 percent of the animals whose mean temperatures differ the most from the group mean, or by rejecting animals whose mean temperatures differ by more than 1.28 standard deviations from the group mean, the animals likely to produce poor meat quality were detected. In this example, the actual rejection rate was 17%.

All publications mentioned in this specification are indicative of the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be obvious that certain changes and modifications may be practised within the scope of the appended claims.

LIST OF REFERENCES

Clark, J. A. and Cena, K. 1972. Thermographic measurements of the surface temperatures of animals. J. of Mammalogy 54: 1003–1007.

Lamarque, J. L., Senac, J. P., Russi, M., Pasqual, J., Respand, G. 1975. Romieu, M. and Jordan, J. Étudthermographique experimentale en pathologic artevielle peripherique. Ann. Radiol. 18: 513–523.

Kenny, F. J. and Tarrant, P. V. 1987. The physiological and behavioural responses of crossbred Friesian Steers to shorthaul transport by road. Lives. Prod. Sci. 17:63–75.

Stephens, D. B. 1980. Stress and its management in domestic animals: A review of behavioural and physiological studies under field and laboratory situations. Adv. Vet Sci. Comp. Med. 24:179–210.

Frens, J. 1975. The influence of skin temperature on thermoregulation. In N. J. M. A. Tilburg, M. G. Strasbourg and E. F. J. R. Both (Ed.) Thermography. S. Karger, Basel P. 218–223.

Houdas, Y. and Guieu, J. D. 1975. Environmental Factors affecting skin temperatures. In. N. J. M. A. Tilburg, M. G. Strasbourg and E. F. J. R. Both (Ed.) Thermography. S. Karger, Basal P. 157–165.

Jones, S. D. M., Schaefer, A. L., Tong, A. K. W., and Vincent, B. C., 1988. The effects of fasting and transportation on beef cattle. 2. Body component changes, carcass composition and meat quality. Lives. Prod. Sci. 20: 25–35.

Warris, P. 1986. Live animal marketing effects on carcass and meat quality. Proceedings P 7–41. In. Work Planning Meeting and meat quality. Agric. Can. R. P. S., Ottawa.

Gariepy, C. J., Amiot, J. and Nada, S. 1987. Early prediction of PSE and DFD by infrared thermography on Live animals. Proc. 33rd Int. Cong. Meat Sci. Tech. II 403–405.

Schaefer, A. L., Jones, S. D. M., Tong, A. K. W., and Vincent, B. C. 1988. The effects of fasting and transportation on beef cattle. 1. Acid—base electrolyte balance and infrared heat loss of beef cattle. Lives. Prod. Sci. 20: 15–24.

Schaefer, A. L., Jones, S. D. M., Murray, A. C., Sather, A. P., and Tong., A. K. W. 1989. Infrared thermography of pigs with known genotypes for stress susceptibility in relation to pork quality. Can. J. Anim. Sci. 69: 491–495.

Schaefer, A. L., Jones, S. D. M., Tong, A. K. W., and Vincent, B. C. 1987a. The effects of fasting and transport on acid-base balance, infrared heat loss and muscle quality of beef cattle. Can. J. Anim. Sci. 67:1182.

Schaefer, A. L., Jones, S. D. M., Murray, A. C., Sather, A. P., and Tong, A. K. W. 1987b. Infrared thermography in three lines of pigs. Can. J. Anim. Sci. 67:1181

Haywood, J. A., Eckerson, J. D. and Coilis, M. 1975. Thermal balance and survival time prediction of men in cold water. Can. J. Physiol. Pharmacol. 53: 21–32.

Jones, S. D. M. and Tong, A. K. W. 1989. Factors influencing the commercial incidence of dark cutting. Can. J. Anim. Sci. 69: 649–654.

Sather, A. P. and Murray, A. C. 1989. The development of a halothane sensitive line of pigs. Can. J. Anim. Sci. 69: 323–331.

Murray, A. C. and Sather, A. P. 1986. Characteristics of the meat quality of a halothane-positive line of swine. Can. J. Anim. Sci. 66:1168.

Agriculture Canada Publication, 1984. Pork Quality, A guide to understanding the colour and structure of pork muscle. Pub. 5180. B. Ottawa.

Mitchell, G. and Heffron, J. J. A. 1982. Porcine stress syndromes, Advances in Food Research, Vol. 28, p. 167–230, ed. C. O. Cheschester, et al., Academic Press, New York.

Steel, R. G. D. and Torrie, J. H., 1980, 2d Edition, Principles and Procedures of Statistics, A Biometrical Approach, McGraw Hill, New York.

We claim:

1. A method for detecting those animals from a group of live domestic animals which have a high probability of producing poor meat quality, comprising:

scanning an area of each animal of the group of live domestic animals with an infrared camera to produce a thermographic image for each animal;

for each animal's thermographic image, determining a measure of central tendency for the temperature;

for the images from the group of live domestic animals, determining a measure of central tendency for the temperatures from all of the images; and rejecting as animals having a high probability of producing poor meat quality, up to twenty percent of the animals, the rejected animals being those whose measures of central tendency differ the most from the measure of central tendency for the group.

2. The method as set forth in claim 1, wherein the measure of central tendency for the temperature determined for each animal's image and for the group images is a mean temperature.

3. The method as set forth in claim 2, wherein the mean temperature for each image is determined from an average pixel temperature for a consistent area of the animal scanned.

4. The method as set forth in claim 3, which includes the further step of, for the images from the group of live domestic animals, determining the standard deviation from the group mean temperature, and using the standard deviation to reject the up to twenty percent of the animals.

5. The method as set forth in claim 1, which includes the further step of, for the images from the group of live domestic animals, determining a measure of dispersion from the measure of central tendency for the group, and using that measure of dispersion to reject the up to twenty percent of animals.

6. A method for detecting those animals from a group of live domestic animals which have a high probability of producing poor meat quality, comprising:

scanning an area of each animal of the group of live domestic animals with an infrared camera to produce a thermographic image for each animal;

for each animal's thermographic image, determining a mean temperature;

for the images from the group of live domestic animals, determining a group mean temperature and a standard deviation from the group mean temperature; and rejecting each animal as one having a high probability of producing poor meat quality if the mean temperature for that animal differs from the mean temperature for the group by more than 0.9 times the standard deviation.

7. The method as set forth in claim 6, wherein the mean temperature for each image is determined from an average pixel temperature for a consistent area of the animal scanned.

8. The method as set forth in claim 7, wherein the animals are live swine.

9. The method as set forth in claim 8, wherein the group of animals is a group having a mean temperature above or below 24°–26° C.

10. The method as set forth in claim 8, wherein the dorsal surface of the animal is scanned.

11. The method as set forth in claim 10, wherein the animal is scanned between the atlas vertebrae and the thoracic vertebrae.

12. The method as set forth in claim 10, wherein the animal is scanned between the atlas vertebrae and the cervical vertebrae.

13. The method as set forth in claim 10, wherein the animal is scanned in the intrascapular area between the atlas vertebrae and the cervical vertebrae.

14. The method as set forth in claim 7, wherein each animal is rejected if the mean temperature for that animal differs from the mean temperature for the group by more than 1.28 times the standard deviation.

15. The method as set forth in claim 14, wherein the animals are live cattle or elk.

16. The method as set forth in claim 15, wherein the dorsal surface of the animal is scanned.

17. The method as set forth in claim 16, wherein each animal is scanned between the atlas vertebrae to the thoracic vertebrae.

18. The method as set forth in claim 17, wherein the animals are cattle.

19. The method as set forth in claim 18, wherein each animal is scanned from the side.

20. The method as set forth in claim 19, wherein the scan includes one or more of the head, trunk and extremities of the animal.

21. The method as set forth in claim 18, wherein the group of animals is a group having a mean temperature above or below a temperature range of 28°–32° C.

22. The method as set forth in claim 7, wherein each animal is scanned in an antemortem environment.

23. The method as set forth in claim 22, wherein each animal is scanned within about 6 hours of a transport or within 24 hours of slaughter.

* * * * *